United States Patent [19]

Kambara et al.

[11] Patent Number: 5,307,148
[45] Date of Patent: Apr. 26, 1994

[54] FLUORESCENCE DETECTION TYPE ELECTROPHORESIS APPARATUS

[75] Inventors: Hideki Kambara, Hachiouji; Keiichi Nagai, Higashiyamato; Tamotu Simada, Akishima; Tetsuo Nishikawa, Itabashi; Tomoaki Sumitani, Hachiouji, all of Japan

[73] Assignee: Hitachi, Ltd., Tokyo, Japan

[21] Appl. No.: 684,113

[22] Filed: Apr. 12, 1991

Related U.S. Application Data

[63] Continuation-in-part of Ser. No. 505,323, Apr. 5, 1990, abandoned.

[30] Foreign Application Priority Data

Apr. 12, 1990 [JP] Japan .................................. 2-95063

[51] Int. Cl.$^5$ ............................................. G01N 21/64
[52] U.S. Cl. ..................................... 356/344; 356/417
[58] Field of Search ............... 356/344, 317, 318, 417; 250/458.1; 204/299 R; 422/82.07, 82.08; 436/172

[56] References Cited

U.S. PATENT DOCUMENTS

| | | | |
|---|---|---|---|
| 4,243,318 | 1/1981 | Stohr | 356/39 |
| 4,832,815 | 5/1989 | Kambara et al. | 204/182.8 |
| 4,881,812 | 11/1989 | Ohkubo et al. | 356/344 |
| 5,062,942 | 11/1991 | Kambara et al. | 250/458.1 |

FOREIGN PATENT DOCUMENTS

| | | | |
|---|---|---|---|
| 148946 | 6/1989 | Japan | 356/344 |
| 203255 | 8/1990 | Japan | 356/344 |

OTHER PUBLICATIONS

"Science", vol. 238, pp. 336–341 (Oct. 16, 1987).
"Nature", vol. 321, pp. 674–679 (Jun. 12, 1986).

*Primary Examiner*—Richard A. Rosenberger
*Attorney, Agent, or Firm*—Pennie & Edmonds

[57] ABSTRACT

A multicolor fluorescence detection type electrophoresis apparatus comprises an electrophoretic device having migration lanes in which fragment groups specifically labeled by fluorophores of different light emission peak wavelengths are mixed, added, and migrated. It identifies and detects the fragment groups. It uses laser beams of different wavelengths for exciting the fluorophores in the migration lanes. The laser beams are irradiated to separate positions on the migration lanes for detection of a few kinds of fluorophores at irradiation positions. For the purpose, multicolor optical filters are arranged near the irradiation positions to identify and detect lights emitted from the fluorophores excited by wavelength at every irradiation position.

13 Claims, 5 Drawing Sheets

FLUORESCENCE DETECTION TYPE ELECTROPHORESIS APPARATUS

SPECIFIC REFERENCE TO THE EARLIER FILED APPLICATION

This application is a continuation-in-part application of our pending U.S. patent application Ser. No. 07/505,323 filed Apr. 5, 1990, now abandoned which corresponds to the Japanese Patent Application 01-90844, and our pending U.S. patent application Ser. No. 07/506,986 filed patent applications 01-90843, 01-90845, and 01-218582. Disclosures of the U.S. patent applications are hereby incorporated herein by reference.

BACKGROUND OF THE INVENTION

The present invention relates to a multicolor fluorescence detection type electrophoresis apparatus, and more particularly concerns a multicolor fluorescence detection type electrophoresis apparatus preferable for analysis of DNA, RNA, and protein labeled by fluorescent dyes, and in particular for sequence analysis of DNA or genetic diagnostics.

Determination of DNA base sequence has been conventionally made by way of auto-radiography. Recently, real time detection systems having fluorescent labels used have been developed. In a system disclosed in the "Science", Vol. 238, pp 336-341 (1987), DNA fragments are labeled with four kinds of fluorophore corresponding to every four terminus species, and mixed and injected in a single migration lane for analysis. The disclosed system is a multicolor labeling analysis system. The migration lane has a laser beam irradiated at a measuring position to excite the fluorophores. Lights emitted from the fluorophores are detected by two detectors having a filter, each of which having a different transmission band, thereby distinguishably detecting the four kinds of fluorophore, or the four terminus species.

A similar multicolor labeling analysis system was disclosed in the "Nature", Vol. 321, pp 674-679. In the system, laser beam line of 488 or 514 nm is selected and irradiated to a measurement position in a time sharing way for effective excitation of the four kinds of fluorophore. An emission wheel further is provided in front of a light-sensitive detector to switch over four kinds of filters to select a wavelength so that the four kinds of fluorophore, or the four terminus species can be distinguishably detected.

On the other hand, the U.S. pat. Ser. No. 4,832,815 filed Oct. 18, 1988, discloses a multicolor labeling analysis system capable of distinguishing a plurality of fluorophores by using a direct-vision prism and a two-dimensional light-sensitive detector which are combined to optically disperse lights from a light emitting line on a migration gel.

SUMMARY OF THE INVENTION

In general, a labeling fluorophore has a wide band emission spectrum. It therefore often happens that the light emission spectra of a plurality of fluorophores overlap one another even if they are different in the selected peak wavelengths. This means that the analysis system having the direct-vision prism used involves a disadvantage of very limited combination of the fluorophores available enough to distinguish.

It is necessary to make the distance between the objective and the detector long for obtaining enough wavelength dispersion in the direct vision prism system. It results in a disadvantage of low detection sensitivity due to a small light receiving angle.

On the other hand, the system that has the filter in front of the light-sensitive detector can be improved by way of proper selection of the filter both in the distinguishability and availability of the light as compared with the one having the direct-vision prism. However, with increase of samples to distinguish, or with increase of the number of fluorophores, it occurs that the scattered excitation light for one fluorophore may interrupt the detection of other fluorophores. This results in the disadvantage that the sensitivity of the fluorophoretic analysis is lowered or sometimes the DNA detection becomes impossible due to the scattering signals.

As mentioned above, the conventional multicolor fluorescence detected type electrophoresis apparatuses are limited in the number of the fluorophores used, or the number of the samples mixed to flow together the same migration lane to obtain enough electrophoresis resolution and high analytical sensitivity. In fact, only two to four fluorophores have been distinguished.

In view of the foregoing, an object of the present invention is to provide a multicolor fluorescence detection type electrophoresis apparatus that can distinguish an increased number of fluorophores, which leads to an improved efficiency of the electrophoretic analysis.

Another object of the present invention is to provide a multicolor fluorescence detection type electrophoresis apparatus that is advantageous in the resolution of the electrophoretic analysis.

Further object of the present invention is to provide a multicolor fluorescence detection type electrophoresis apparatus that can distinguish a plurality of fluorophores accurately.

Briefly, the foregoing objects are accomplished in accordance with aspects of the present invention by a multicolor fluorescence detection type electrophoresis apparatus that consists of at least an excitation light source, an electrophoresis separation gel plate, and a fluorescent light detector, wherein the excitation light source is a light source emitting a plurality of excitation lights of different wavelengths, and the plurality of excitation lights can irradiate different positions separated a predetermined distance apart on the electrophoresis separation gel plate, and a plurality of fluorescent images obtained by the irradiation of the plurality of excitation lights to the different positions separated, by the predetermined distance apart on the electrophoresis separation gel plate can be individually focused on different positions of the fluorescence detector.

A typical multicolor fluorescence detection type electrophoresis apparatus according to the present invention comprises excitation sources, for example, of a laser beam of a first excitation wavelength of 488 nm being irradiated to a first position on a migration lane, and another laser beam of a second excitation wavelength of 532 nm being irradiated to a second position on the migration lane. The migration lane has a sample mixture, for example, of eight kinds of sample added therein before the electrophoresis analysis. The first to fourth samples of the sample mixture are fragment families individually labeled by the first to the fourth fluorophores having different emission wavelengths, respectively. They cannot be substantially excited by the second excitation light, but effectively excited by the first excitation light. The fifth to eighth samples in the sample mixture are fragment families individually labeled with the fifth to eighth fluorophores having different emission wavelengths, respectively. They cannot be substantially excited by the first excitation light, but effectively excited by the second excitation light.

Therefore, when the first to fourth samples of fragment families reach the first position of migration lane, the first position emits the fluorescent lights of the respective wavelengths. These fluorescences can be detected without being disturbed by scattering light of the second excitation light source because the irradiation position of that is quite different from the latter. When the fifth to eighth samples of fragment families reach the second position of migration lane, the second position emits the fluorescent lights of the respective peak wavelengths. There is provided a fluorescent detector capable of distinguish the wavelengths in the vicinity of the first position of the migration lane which is free from the disturbance of the second excitation light. There also is provided another fluorescent detector capable of distinguishing the wavelengths in the vicinity of the second position of the migration lane, which is also operated free from the disturbance of the first excitation light.

A change of signal of each wavelength output of the two fluorescent detectors with time shows a distribution of fragment lengths of the fragment groups contained in the first to eight samples.

An advantage of the construction of the present invention described above is that the plurality of fluorophore groups can select an excitation source of proper wavelength each. It also can excite numbers of fluorophores at a high efficiency. It further can accurately identify the number of fluorophores as these can be easily identified at the respective emission positions.

A practical construction according to the present invention comprises a single electrophoresis plate having a plurality of parallel migration lanes, a first laser beam irradiation arrangement as an excitation source is set so as to cross the migration lane from a first position of a side edge parallel to the migration lane of the electrophoresis plate, and a second laser beam irradiation arrangement as another excitation source is set so as to cross the migration lane from a second position of the side edge parallel to the migration lane of the electrophoresis plate. Light detecting arrangements for identifying and detecting the fluorophores are provided in the vicinity of the irradiation positions of the first and second laser beams, respectively. Each of the light detecting arrangement comprises a first and second image dividing devices for dividing the fluorescent image into a plurality of virtual images, an optical system for refocusing the plurality of divided virtual images on a detector, a filtering device for wavelength selecting each of the lights divided and emitted out of the image dividing device, and a light detecting device for distinguishing and detecting a plurality of refocused fluorescent images with respect to position. It is matter of course that a wavelength selection characteristic of each area of the filtering device is chosen on the basis that the lights emitted from the plurality of fluorophores excited by the first laser beam can be distinguished and the lights emitted from the plurality of fluorophores excited by the second laser beam can be distinguished.

An advantage of the apparatus having the image dividing devices and the filtering devices for wavelength selecting each of the divided and emitted lights, is that continuous detection of every fluorescence can be made without time sharing. Alternatively, the image dividing devices can be replaced by rotary multicolor filters or similar devices that can choose and insert a plurality of filters between the light detecting devices and the light emitting positions.

Further alternatively, the irradiating devices for emitting the laser beams to cross the plurality of migration lanes can be replaced by irradiating devices of which laser beams can scan a predetermined detection line on the electrophoresis separation gel plate. In operation, the irradiating devices are made so that the first and second laser beams can scan on the detection line while a predetermined distance can be kept between the points irradiated by both excitation beams. This separation of the irradiation points is useful for eliminating the scattered lights from the rest of the excitation beam.

The fluorescent detection devices each have a rotary multicolor filter and a first and second photoelectric multipliers which can move with the irradiation points in the vicinity of the detection line, respectively.

In the arrangements described above, the number of the excitation lights irradiated to the different positions can be increased to three or more.

The multicolor fluorescence detected type electrophoresis apparatus of the present invention described above can analyze the DNA or RNA base sequence or protein. Determination of the DNA or RNA base sequence can be made as follows. Firstly, a plurality of DNA samples are cloned in different vectors, which are amplified to obtain numbers of cloned DNAs. These are denatured into single-stranded NDAs, which are mixed together. It is made to prepare a plurality of kinds of primers uniquely hybridized to vectors and labeled with different fluorophores. The primers are added to those mixtures. The mixed solution is divided into four parts. Each of the parts is individually subjected to the known synthesis of complementary strand so that their respective terminus base species become adenine (A), cytosine (C), guanine (G), and thymine (T). This obtains four fragment groups to be used to detect positions of A, C, G, and T (or T, G, C, A of the template DNA samples). It should be noted that the fragment groups are all labeled with the fluorophores different for every template DNA sample. Each of the fragment groups can be subjected into the four respective migration lanes of the multicolor fluorescence detected type electrophoresis apparatus of the present invention which can identify the fluorophores so that each of the DNA base sequences can be determined. If the apparatus is constructed so as to be capable of identifying eight kinds of fluorophores, as an example, determination of the base sequences of eight kinds of DNA samples can be executed by one time of migration in the four migration lanes.

On the other hand, if fragment families labeled with fluorophores different for every kind of terminus species are prepared, the fragment families can be mixed and subjected to one migration lane. In other words, it is possible to execute by one time of migration the determination of base sequences of the DNA samples the number of which is same as that of the migration lanes provided in the electrophoresis separation gel plate.

DETAILED DESCRIPTION OF THE PREFERRED EMBODIMENTS

Figure 1:
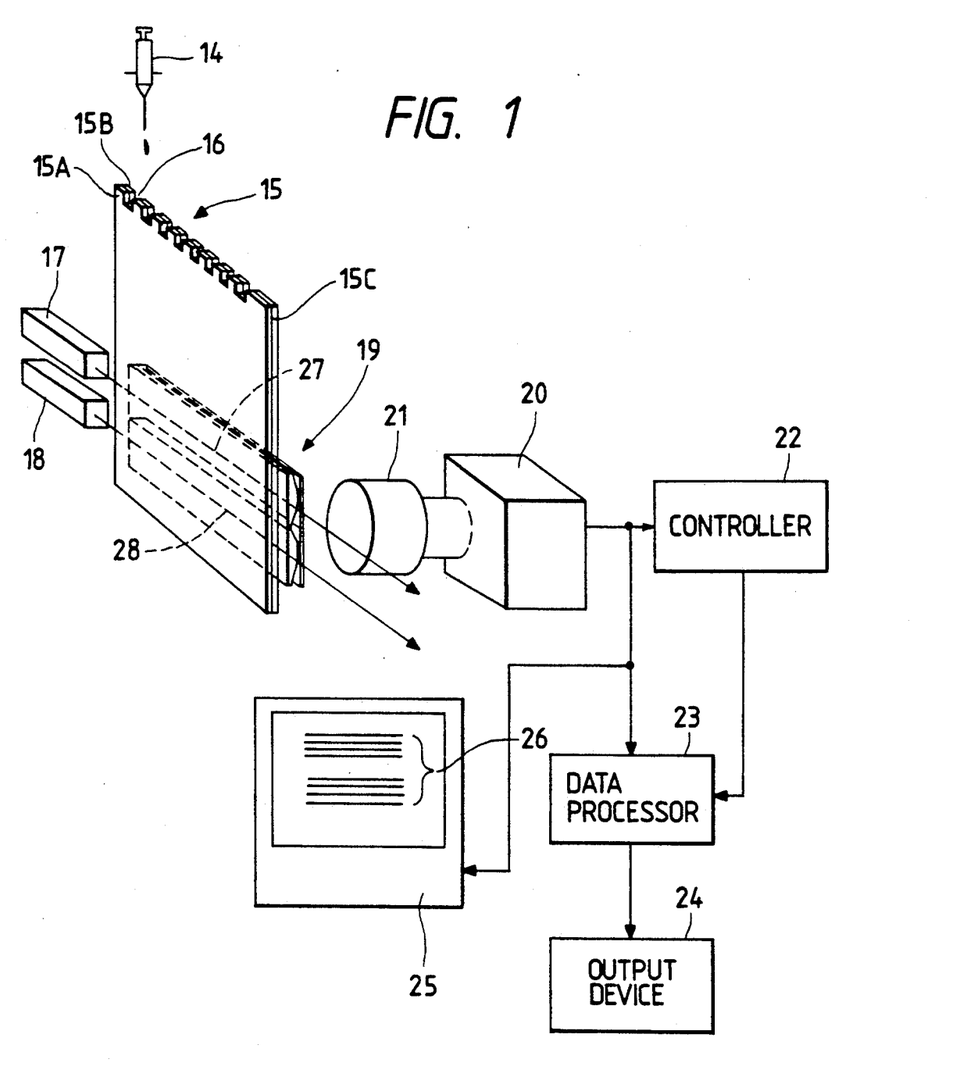
FIG. 1 is a block diagram illustrating an embodiment of a multicolor fluorescence detected type electrophoresis apparatus according to the present invention.

The present invention is illustrated in further detail by reference to the accompanying drawings. FIG. 1 is an embodiment of the multicolor fluorescence detected type electrophoresis apparatus according to the present invention. In the figure, a gel electrophoretic plate 15 comprises a pair of quartz gel supporting plates 15A and 15B of 200 mm wide, 300 mm long, and 5 mm thick facing each other with a gap around 0.3 mm and a gel plate 15C of 4.5% polyacrylamide inserted in the gap for electrophoresis separation (also see FIG. 2). The gel electrophoretic plate 15 has a predetermined number of sample loading wells 16 at a top thereof. The samples are put into wells by a sample injecting jig 14.

A whole top of the gel plate 15C is dipped into a top buffer solution vessel (not shown). A whole bottom of the gel plate 15C also is dipped into a bottom buffer solution vessel (not shown). An electrophoresis voltage is applied between the two buffer solution vessels. This allows downward migration of the fragments in the sample solution injected in the sample wells 16. The gel plate 15C therefore has a plurality of migration lanes formed in parallel corresponding to positions of the sample wells 16.

Figure 2:
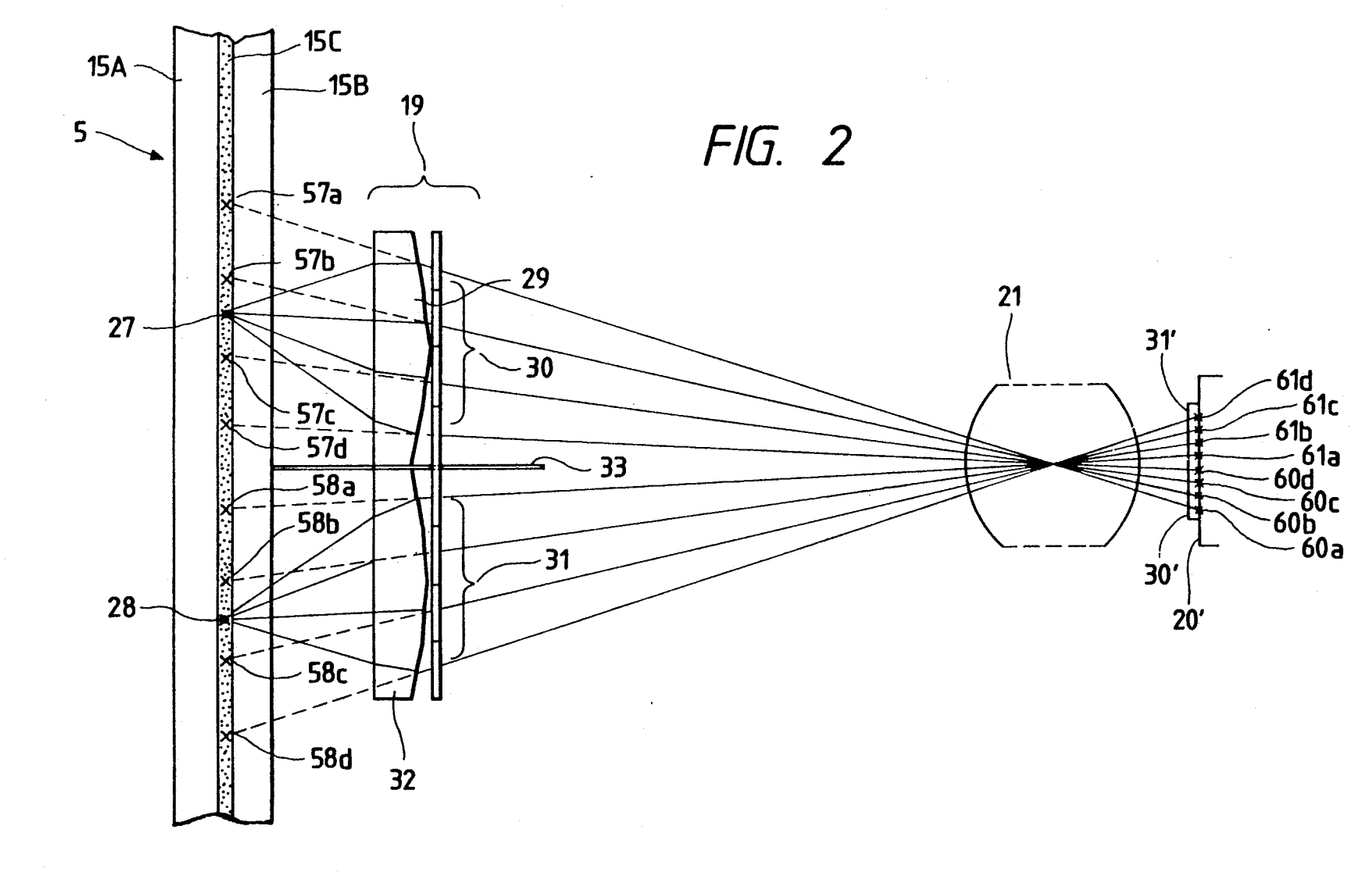
FIG. 2 is a cross sectional view illustrating major section of the embodiment.

The gel electrophoretic plate 15 has a laser beam of 488 nm wavelength irradiated to one side edge, which is a first position at an edge parallel with the migration lanes, by an argon laser 17 which is an excitation light source. The gel electrophoretic plate 15 also has a laser beam of 532 nm wavelength irradiated to a second position at the edge lower than the first position by a YAG laser 18. The laser beams irradiated by the argon laser 17 and the YAG laser 18 horizontally pass through light paths 27 and 28 in the gel plate 15C respectively, as shown in FIGS. 1 and 2. The laser beams therefore cross across the plurality of migration lanes in the gel plate 15C. The light path 27 is positioned, for example, at 25 cm lower than bottoms of the sample wells 16. The light path 28 is positioned at 1 cm further lower than the light path 27.

A fluorescent line image is produced on the light paths 27 and 28, and is detected by a two-dimensional fluorescent detector 20. There is aligned an image dividing optical system 19 between the gel electrophoretic plate 15 and a lens 21 which focuses the image on a two-dimensional fluorescent detector 20.

FIG. 2 is a detailed structure of the image dividing optical system 19. The image dividing optical system 19, as shown in the figure, includes a polygonal prism 29 having one light receiving surface for receiving a fluorescent light emitted on the light path 27 and four light emitting surfaces and another polygonal prism 32 having one light receiving surface for receiving a fluorescent light emitted on the light path 28 and four light emitting surfaces. The two polygonal prisms are light shielded from each other by a separator.

The polygonal prism 29 is aligned so that its four light emitting surfaces can all be in parallel with the light path 27. As the light emitting surfaces direct differently, lights are differently refracted in the lens 21. In other words, the fluorescent line image produced at the position of the light path 27 is divided into four images 57a, 57b, 57c, and 57d as viewed through the lens 21. The polygonal prism 29 divides the fluorescent line image produced at the position of the light path 27 into the four virtual images. The two-dimensional fluorescent detector 20 therefore has four line images 60a, 60b, 60c, and 60d focused on a detection surface 20' thereof, which correspond to the respective four virtual images. Similarly, the polygonal prism 32 features in dividing the fluorescent line image produced at the position of the light path 28 into the four virtual images 58a, 58b, 58c, and 58d. The two-dimensional fluorescent detector 20 therefore has four line images 61a, 61b, 61c, and 61d focused on a detection surface 20' thereof, which correspond to the respective four virtual images.

There are aligned multicolor filters 30 and 31 adjacent to the light emitting surfaces of the respective polygonal prisms 29 and 32. The multicolor filter 30 can distinguish four lights emitted from four fluorophores one another from among fluorescent lights labeling the sample fragment group excited by the argon laser of 488 nm. The multicolor filter 30, in other words, has four color areas corresponding to the four light emitting surfaces of the polygonal prism 29 so that it can transmit only light waves adjacent to peak wavelengths of the four respective lights excited from the four fluorophores. The line images 60a, 60b, 60c, and 60d formed on the detection surface 20' correspond to the four lights emitted from the fluorophores on the light path 28. Similarly, the multicolor filter 31 has four color areas corresponding to the four light emitting surfaces of the polygonal prism 32 so that it can distinguish four different lights emitted from four different fluorophores excited by the YAG laser of 532 nm.

As described above, the present embodiment is arranged so that the two kinds of exciting beam is irradiated to the different positions on the electrophoretic plates, and the images at the respective irradiation positions are further divided for wavelength selection in order for the two-dimensional fluorescent detector 20 to have the eight fluorescent line images focused on the detection surface thereof which correspond to the lights emitted from the eight fluorophores.

The fluorescent line images 26 are converted to electric signals, which are not only displayed on a monitor 25, but also fed to a controller 22 and a data processor 23. The data processor 23 records change of the fluorescent line image intensities with time corresponding to process of the electrophoresis. It also performs the necessary process for analysis, and feeds results to an output device 24 such as a printer.

The embodiment described above does not always have the multicolor filters 30 and 31 arranged close to the light emitting surfaces of the polygonal prisms. Alternatively, as an example, as indicated at 30' and 31' in FIG. 2, they can be aligned in the vicinity of the detection surface 20' of the two-dimensional fluorescent detector 20. In short, the multicolor filters 30 and 31 may be provided at positions where the light paths to the fluorescent line images 60a through 60d and 61a through 61d refocused of the fluorescent line images 27 and 28 cannot overlap one another.

The construction that the divided fluorescent line images 60a through 60d and 61a through 61d are detected by a single two-dimensional fluorescent detector can be replaced alternatively as follows. The four fluorescent line images divided by the polygonal prism 29 and the different four fluorescent line images divided by the polygonal prism 32 may be refocused by different lenses and detected by different two-dimensional fluorescent detectors.

Further alternatively, the eight fluorescent images may be detected by eight line sensors.

Figure 3:
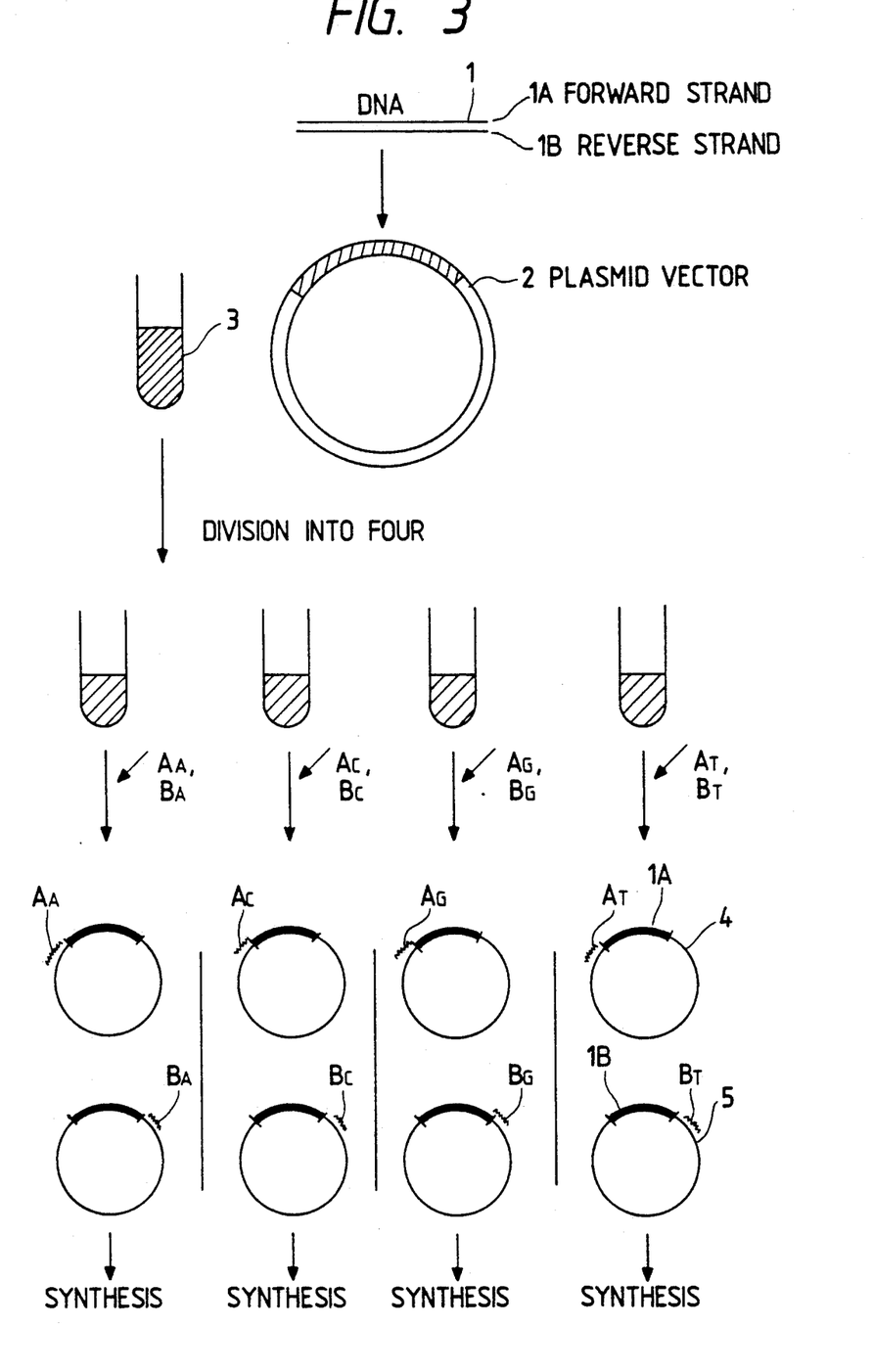
FIGS. 3 and 4 are illustrations showing how to prepare samples subjected to the apparatus of the present invention.
Figure 4:
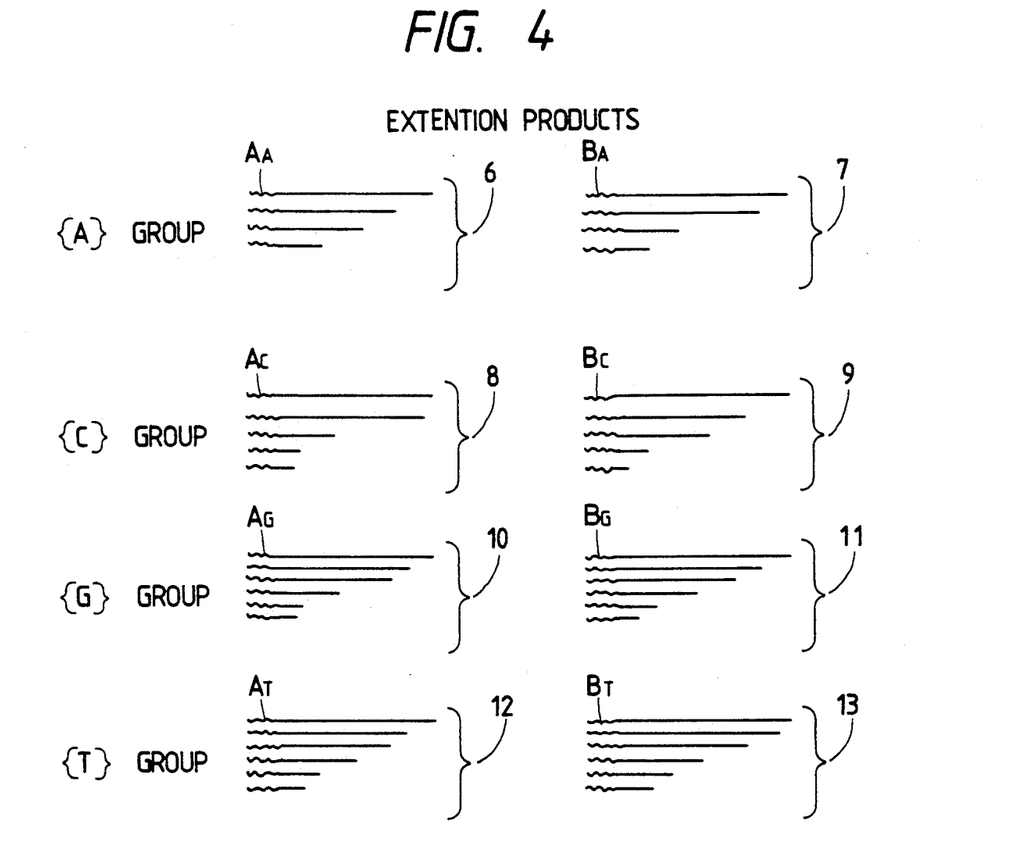

In turn, the following describes an example of the multicolor fluorescence detection type electrophoresis apparatus described above applied to determine a DNA base sequence as to its operation and function by reference to FIGS. 3 and 4. In the example, a double stranded DNA, the base sequence of which is to be determined, is denatured into two kinds of single stranded DNA to determine the DNA base sequence from each terminal 5' of positive and negative strands. Firstly, as shown in FIG. 3, an objective DNA is cloned in a plasmid vector 2 and amplified to obtain many copies of the plasmid. These are denatured into single stranded DNA in an ordinary method such as an alkaline denature process. A sample solution 3 obtained is a mixture of a vector 4 having the forward DNA base sequence 1A of the objective DNA 1 examined and a vector 5 having the reverse DNA base sequence 1B of the DNA sample 1.

The sample solution 3 is equally divided into four fractions. The insert region of each vector is used as template to form a fragment group to be examined in the electrophoresis apparatus. For the purpose, firstly, eight kinds of oligonucleotid primers are prepared. These are represented by $A_A$, $A_C$, $A_G$, $A_T$, $B_A$, $B_C$, $B_G$, and $B_T$. Each of the primers $A_A$, $A_C$, $A_G$, and $A_T$ contains the oligonucleotid which is uniquely hybridized on 5' terminus part at the insert part of the light receiving surface 4 having the forward strand 1A, and is individually labeled by one of the four fluorescent pigments excited by the argon laser of 488 nm. The fluorescent dyes include four kinds of succinyl fluorescien such as called SF-505, SF-512, SF-519, and SF-526. The center emission wavelengths of the dyes are 505, 512, 519, and 526 nm, respectively. A method of preparation of the labeled origonucleotid primers is described in the "Science", Vol. 238, pp 336-341 (1987).

On the other hand, each of the primers $B_A$, $B_C$, $B_G$, and $B_T$ contains the oligonucleotide which is uniquely hybridized on 5' terminus part at the inserted part of the vector 5 having the reverse strand 1B, and is individually labeled by one of the four fluorescent pigments excited by the YAG laser of 532 nm. The fluorescent dyes include, for example, eosin-5-isothiocyanate, tetramethyl rhodamine isothiocyanate (TRITC), rhodamine X isothiocyanate (XRITC), and texas red. The center emission wavelengths of the dyes are 560, 570, 610, and 620 nm, respectively.

The primers $A_A$ and $B_A$ are mixed to a first one of the four divided sample fraction. To it further added are deoxynucleotide and dideoxnucleotide mixed so that the synthesized strand can be terminated at adenine. It is processed to produce a primed synthesis by an enzymatic reaction.

A second sample fraction has the primers $A_C$ and $B_C$ mixed therein, a third sample fraction has the primers $A_G$ and $B_G$ mixed therein, and a fourth sample fraction has the primers $A_T$ and $B_T$ mixed therein. They are processed to produce complementary strand synthesis by an enzymatic reaction so that the respective synthesized strands can be terminated at cytosine, guanine, and thymine, respectively.

The synthesized strands are denatured and separated from the vectors to make sample families {A}, {C}, {G}, and {T}. As shown in FIG. 4, therefore, the sample family {A} contains fragments 6 of various lengths indicating positions of adenine on the forward strand 1A and a fragments 7 of various lengths indicating positions of adenine on the reverse strand 1B. Similarly, the sample family {C} contains fragments 8 and 9 indicating individual positions of cytosine on the forward strand 1A and reverse strand 1B, the sample family {G} contains fragments 10 and 11 indicating individual positions of guanine on the forward strand 1A and reverse strand 1B, and the sample family {T} contains fragment groups 12 and 13 indicating individual positions of thymine on the forward strand 1A and reverse strand 1B. The fragment groups 6 to 13 are labeled by different fluorescent dyes in the example.

The sample groups {A}, {C}, {G}, and {T} obtained are mixed to a single sample group, which is added for analysis to one migration lane of the electrophoresis apparatus which can identify the fragments with the above mentioned wavelengths. In other words, the DNA base sequences of the DNA samples the number of which is equal to that of the migration lanes provided on the electrophoretic plate can be determined by a single electrophoresis. As the fragments groups are made with respect to the both forward and reverse strands for electrophoresis analysis in this example, further, the number of the DNA base sequences determined is up to 1000 by a single electrophoresis, while it is up to 400 or 500 by the convention electrophoresis apparatus.

Alternatively, the above mentioned analysis method can be replaced by the one in the electrophoresis apparatus that the fragment groups are labeled with a plurality of fluorescent dyes which are different for every DNA sample and not distinguished in the kinds of terminus species. For example, the eight DNA samples are incorporated into the respectively different plasmid vectors, and is subjected to cloning to denaturalize to single strand vector. On the other hand, eight kinds of the oligonucleotid which is uniquely hybridized with individual vectors are prepared. As the primers for them are used the ones labeled with the eight kinds of fluorescent dyes mentioned in the above example. The single strand vectors and the eight kinds of primer are mixed in a single vessel to cause a hybridization reaction. In turn, the sample is divided into four parts as in the above example. For each of the parts is made the primed synthesis so that the terminus species are made different. They are isolated to obtain four fragment groups. In this case, the four kinds of sample the terminal species of which are made different as prepared by the primed synthesis are not mixed, but added to the different migration lanes before the electrophoresis analysis.

With the combination of the plurality of kinds of plasmid vectors and the plurality of kinds of oligonucleotide primer singularly hybridizing with them as described above, the cloning and hybridization reactions can be made in the respective single vessels. This saves labor of sample preparation.

In the embodiment described above, the electrophoresis plate has two exciting beams of different wavelengths irradiated to the two positions thereof for identification of the eight kinds of fluorescent dye. In this case, as the four fluorescent dyes are identified from among the fluorescent lights emitted at the first irradiation position 27, and the remaining four fluorescent dyes are identified from among the fluorescent lights emitted at the second irradiation position 28, it is easy to eliminate stray laser lights in the fluorescence detection.

In order to accomplish such elimination, it is preferable to select and combine such exciting lights and fluorophores that the plurality of fluorophores detected at the first irradiation position 27 can be effectively excited by the exciting light irradiated to it, but cannot substantially be excited by the exciting light irradiated to the second irradiation position 28 and conversely, the plurality of fluorophores detected at the second irradiation position 28 can be effectively excited by the exciting light irradiated to it, but cannot substantially be excited by the exciting light irradiated to the first irradiation position 27. Distance between the first and second irradiation positions is preferably 10 mm or more apart.

The embodiment, as described above, makes use of the polygonal prisms for dividing the images. This allows continuous analysis of the fragment groups labeled by the specific fluorophores without replacing the filters.

Alternatively, the three or more irradiation positions of the exciting lights may be provided so that more number of the fluorophores can be identified. It can be constructed, for example, that in addition to the argon laser and the YAG laser shown in FIG. 1, a red He-Ne laser of 633 nm or a diode laser of 670 nm can be provided for light irradiation at a third irradiation position. For the fluorophores having different peak wavelengths emitted at the third irradiation position are available phthalocyanine alminium complexes including, for example, the Ultralite 680 of 682 nm peak wavelength, the Ultralite 700 of 697 nm, and the Ultralite 720 of 717 nm, which are sold by Ultra Diagnostics Co.

Figure 5:
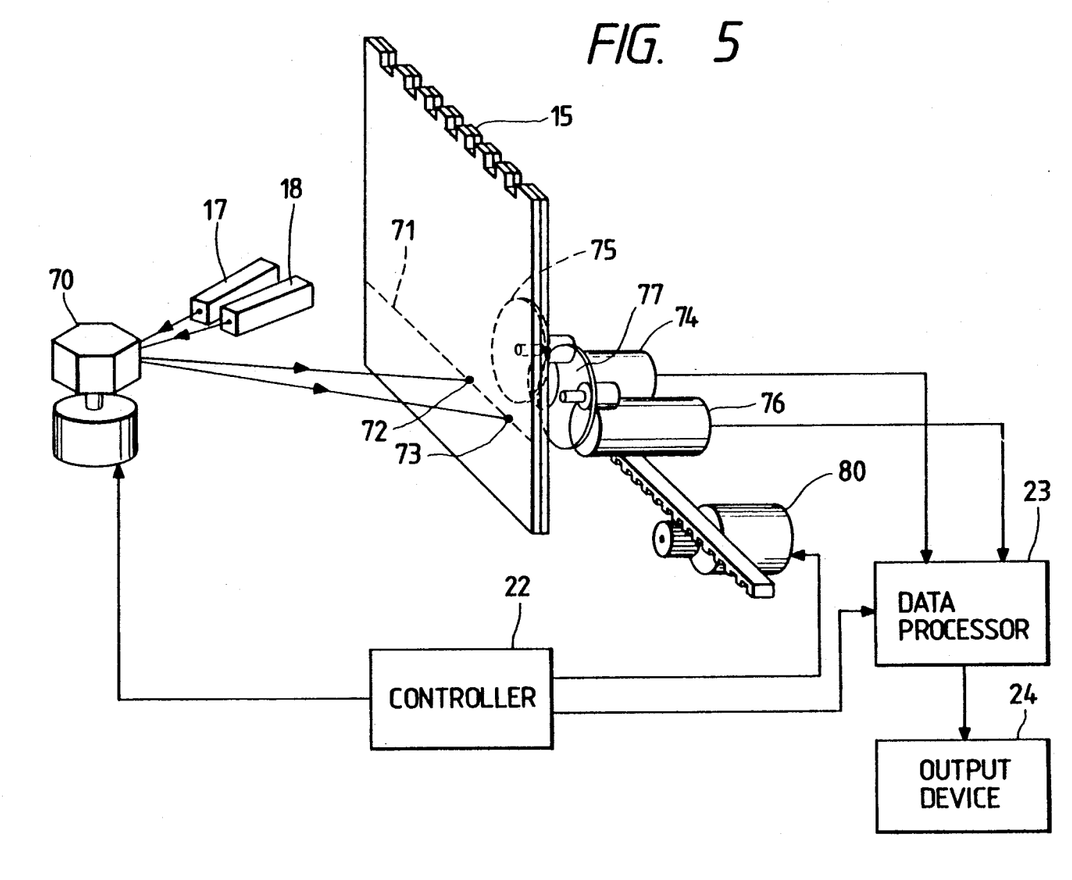
FIG. 5 is a block diagram illustrating another embodiment of the present invention.

Further, another alternative construction can be made to identify the plurality of fluorophores excited at the irradiation positions. FIG. 5 is another embodiment of the present invention in which the laser beams emitted by the argon laser 17 and the YAG laser 18 are irradiated toward one surface of the electrophoretic plate 15 as being scanned by a polygon mirror 70. Irradiation points 72 and 73 are moved with a certain distance on a predetermined detection line 71 crossing a plurality of migration lanes of the electrophoretic plate 15. Fluorescent lights emitted from the fluorophores at the irradiation points are independently detected by photoelectron multipliers 74 and 76.

The photoelectron multipliers 74 and 76 are moved by a drive arrangement 80 connected therewith as the irradiation points 72 and 73 are moved. The photoelectron multipliers 74 and 76 also have rotary multicolor filters 75 and 77 provided thereto, respectively. Each of the rotary multicolor filters has a plurality of color areas divided on its filter plate. The filter plate is rotated in front of a light receiving surface of the photoelectron multiplier so that it can sequentially select the plurality of fluorophores emitting at the irradiation points by way of wavelength selection. In other words, detection signals output of the photoelectron multipliers 74 and 76 are time divided of the lights emitted from the plurality of fluorophores.

The data processor 23 distributes the detection output signals to the plurality of migration lanes according to scanning of the irradiation points 71 and 72 and the positions of the photoelectron multipliers 74 and 76. It further distributes the detection output signals as signals corresponding to the plurality of fluorophores as the rotary multicolor filters 75 and 77.

Such a time division measurement allows identification and detection of the plurality of the mixed fluorophores made to flow on the migration lanes.

In the embodiments described above, if the plurality of fluorophores cannot be identified satisfactorily even by the wavelength selection of the color areas of the multicolor filters, then the detection output signals of the lights passing the color areas are compared with one another to determine which of the fluorophores emits.

What is claimed is:

1. A multicolor fluorescence detection type electrophoresis apparatus, comprising in combination:

electrophoretic means having a plurality of migration lanes for which fragment groups specifically labeled with a plurality of fluorophores of different light emission peak wavelengths migrate electrophoretically in one direction, exciting means for simultaneously irradiating a plurality of light beams of different wavelengths to a plurality of irradiation positions in the migration lane to excite the fluorophores, said exciting means simultaneously irradiating all of said plurality of migration lanes at said plurality of irradiation positions, said plurality of irradiation positions being spaced apart in the migration direction, the fragment groups being excited at each of said plurality of irradiation positions, and light detection means for identifying the detecting lights emitted from the fluorophores excited at the plurality of irradiation positions at each of said irradiation positions.

2. A multicolor fluorescence detection type electrophoresis apparatus according to claim 1, characterized in that the light detection means comprises in combination:

image dividing means for dividing each of fluorescent images formed at said plurality of irradiation positions into a plurality of virtual images at different positions, optical lens means for refocusing the respective divided virtual images, multicolor optical filters for wavelength selecting the respective refocused images, and a light-sensitive detector for identifying and detecting the wavelength selected images.

3. A multicolor fluorescence detection type electrophoresis apparatus according to claim 2, characterized in that said image dividing means comprises a plurality of polygonal prisms corresponding in number to said plurality of irradiation positions, said each prism having one light receiving surface for receiving fluorescent lights from the corresponding irradiation position and a plurality of light emitting surfaces.

4. A multicolor fluorescence detection type electrophoresis apparatus according to claim 1, wherein any two adjacent irradiation positions are spaced apart by at least 1 cm.

5. A multicolor fluorescence detection type electrophoresis apparatus, comprising in combination:

electrophoretic means having a plurality of migration lanes in which fragment groups specifically labeled with a plurality of fluorophores of different light emission peak wavelengths migrate electrophoretically in one direction, exciting means for simultaneously irradiating a first light of first wavelength for effectively exciting fluorophores belonging to a first group of the plurality of fluorophores at a first irradiation position on said plurality of migration lanes, but cannot substantially excite flurophores belonging to a second group, said first light simultaneously irradiating all of said migration lanes at said first irradiation position, and for irradiating a second light of second wavelength for effectively exciting fluorophores belonging to the second group of the plurality of fluorophores at a second irradiation position on said migration lanes, but cannot substantially excite fluorophores belonging to the first group, said second position being spaced apart from said first irradiation position in the migration direction, said second light simultaneously irradiating all of said migration lanes at said second irradiation position, and light detection means for identifying and detecting lights emitted from the fluorophores of the first group in terms of first fluorescent images produced at the first irradiation position, and for identifying and detecting lights emitted from the fluorophores of the second group in terms of second fluorescent images produced at the second irradiation position.

6. A multicolor fluorescence detection type electrophoresis apparatus according to claim 5, characterized in that the light detection means comprises in combination:

image dividing means for dividing the first and second fluorescent images formed at said first and second irradiation positions into a first plurality of virtual images and a second plurality of virtual images, respectively, optical lens means for refocusing the respective divided virtual images, multicolor optical filters for wavelength selecting the respective refocused images, and a light-sensitive detector for identifying and detecting the wavelength detected images.

7. A multicolor fluorescence detection type electrophoresis apparatus according to claim 6, characterized in that said image dividing means comprises a first polygonal prism for dividing said first fluorescent image formed at said first irradiation position of each of said said plurality of migration lanes into said first plurality of virtual images and a second polygonal prism for dividing said second fluorescent image formed at said second irradiation position of each of said plurality of migration lanes into said second plurality of virtual images, each of said first and second polygonal prisms having one light receiving surface for receiving fluorescent light from the corresponding irradiation position and a plurality of light emitting surfaces.

8. A multicolor fluorescence detection type electrophoresis apparatus according to claim 5, wherein said first and second irradiation positions are spaced apart by at least 1 cm.

9. A multicolor fluorescence detection type electrophoresis apparatus, comprising in combination:

a gel electrophoresis plate having a plurality of parallel migration lanes formed therein in which fragment groups specifically labeled with a plurality of fluorophores of different light emission peak wavelengths migrate electrophoretically, exciting means for simultaneously irradiating a plurality of exciting light beams of different wavelengths, said plurality of light beams being irradiated toward a side edge of said gel electrophoretic plate to simultaneously irradiate across all of said plurality of migration lanes along a corresponding number of irradiation lines at different positions which are spaced apart from each other in the direction of the migration lane, the fragment groups being excited at each of said irradiation lines and light detection means for identifying and detecting lights emitted from the fluorophores excited on the plurality of irradiation lines by wavelength at each of said irradiation positions.

10. A multicolor fluorescence detection type electrophoresis apparatus according to claim 9, characterized in that said light detection means comprises in combination:

image dividing means for dividing each of fluorescent images formed at said plurality of irradiation lines into a plurality of virtual images at different positions, optical lens means for refocusing the respective divided virtual images, multicolor optical filters for wavelength selecting the respective refocused images, and a light-sensitive detector for identifying and detecting the wavelength selected images.

11. A multicolor fluorescence detection type electrophoresis apparatus according to claim 10, characterized in that said image dividing means comprises a plurality of polygonal prisms corresponding in number to said plurality of irradiation lines, said each prism having one light receiving surface for receiving fluorescent lights from the corresponding irradiation line and a plurality of light emitting surfaces.

12. A multicolor fluorescence detection type electrophoresis apparatus according to claim 10, characterized in that said light detecting means is a two-dimensional fluorescent light detector having one detection surface for detecting a plurality of fluorescent line images refocused through said optical lens means.

13. A multicolor fluorescence detection type electrophoresis apparatus according to claim 9, wherein any two adjacent irradiation positions are spaced apart by at least 1 cm.

* * * * *